US011471332B2

(12) United States Patent
Locke et al.

(10) Patent No.: US 11,471,332 B2
(45) Date of Patent: Oct. 18, 2022

(54) SYSTEMS, APPARATUSES, AND METHODS FOR NEGATIVE-PRESSURE TREATMENT WITH REDUCED TISSUE IN-GROWTH

(71) Applicant: KCI Licensing, Inc., San Antonio, TX (US)

(72) Inventors: Christopher Brian Locke, Bournemouth (GB); Timothy Mark Robinson, Shillingstone (GB); David George Whyte, Dorset (GB)

(73) Assignee: KCI Licensing, Inc., San Antonio, TX (US)

( * ) Notice: Subject to any disclaimer, the term of this patent is extended or adjusted under 35 U.S.C. 154(b) by 473 days.

(21) Appl. No.: 15/997,923

(22) Filed: Jun. 5, 2018

(65) Prior Publication Data

US 2019/0231600 A1 Aug. 1, 2019

Related U.S. Application Data

(60) Provisional application No. 62/576,498, filed on Oct. 24, 2017, provisional application No. 62/565,754, (Continued)

(51) Int. Cl.
*A61F 13/00* (2006.01)
*A61F 13/02* (2006.01)
(Continued)

(52) U.S. Cl.
CPC .... *A61F 13/00068* (2013.01); *A61F 13/0216* (2013.01); *A61F 13/505* (2013.01); (Continued)

(58) Field of Classification Search
CPC ............ A61F 13/0216; A61F 13/00068; A61F 13/0223; A61F 13/0213; A61F 13/0206; (Continued)

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |

(Continued)

FOREIGN PATENT DOCUMENTS

| AU | 550575 B2 | 3/1986 |
| AU | 745271 B2 | 3/2002 |

(Continued)

OTHER PUBLICATIONS

3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyethylene-Single-Sided-Medical-Tape-63-Liner/?N=5002385+8729793+3294739632&rt=rud; accessed May 21, 2019>.

(Continued)

*Primary Examiner* — Ariana Zimbouski
*Assistant Examiner* — Alessandro R Del Priore

(57) ABSTRACT

A dressing for treating a tissue site with negative pressure includes a manifold having a first surface and a second surface opposite the first surface. The dressing also includes a first layer adjacent to the first surface and a second layer adjacent to the second surface. The first layer and the second layer each include a polymer film. The dressing also includes a plurality of fluid restrictions in the polymer film adjacent to at least the first surface, and a plurality of bonds between the first layer and the second layer. The plurality of bonds defines separable sections of the manifold.

24 Claims, 10 Drawing Sheets

Related U.S. Application Data filed on Sep. 29, 2017, provisional application No. 62/516,550, filed on Jun. 7, 2017, provisional application No. 62/516,540, filed on Jun. 7, 2017, provisional application No. 62/516,566, filed on Jun. 7, 2017.

(51) Int. Cl.
  *A61M 1/00* (2006.01)
  *A61F 13/505* (2006.01)
  *A61F 13/512* (2006.01)

(52) U.S. Cl.
  CPC ..... *A61M 1/90* (2021.05); *A61F 2013/00655* (2013.01); *A61F 2013/5127* (2013.01)

(58) Field of Classification Search
  CPC ........ A61F 2013/00536; A61F 13/0203; A61F 13/0226; A61F 2013/00863; A61F 13/00029; A61F 13/022; A61F 2013/00604; A61F 13/00021; A61F 13/025; A61F 13/512; A61F 2013/00255; A61F 2013/00638; A61F 2013/53081; A61F 13/505; A61F 2013/00655; A61F 2013/5127; A61M 1/0088; A61M 27/00; A61M 1/0058; A61M 1/0001; A61M 3/0283; A61B 46/00
  USPC ........................................................ 604/313
  See application file for complete search history.

(56) References Cited

U.S. PATENT DOCUMENTS

| | | |
|---|---|---|
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,654,060 A | 4/1972 | Goldman |
| 3,682,180 A | 8/1972 | McFarlane |
| 3,826,254 A | 7/1974 | Mellor |
| 3,930,096 A | 12/1975 | Gilpatrick |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,173,046 A | 11/1979 | Gallagher |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,541,426 A | 9/1985 | Webster |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,983,173 A | 1/1991 | Patience et al. |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,313 A | 5/1994 | Karami et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,352 A | 9/1995 | Nishino et al. |
| 5,466,231 A | 11/1995 | Cercone et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,635,201 A * | 6/1997 | Fabo ................ A61F 13/0276 424/443 |
| 5,636,643 A | 6/1997 | Argenta et al. |
| 5,645,081 A | 7/1997 | Argenta et al. |
| 5,720,714 A | 2/1998 | Penrose |
| 5,842,503 A | 12/1998 | Foley |
| 5,951,505 A | 9/1999 | Gilman et al. |
| 5,981,822 A | 11/1999 | Addison |
| 5,998,694 A * | 12/1999 | Jensen ................ A61F 13/023 602/56 |
| 6,019,511 A | 2/2000 | Thomas et al. |
| 6,071,267 A | 6/2000 | Zamierowski |
| 6,135,116 A | 10/2000 | Vogel et al. |
| 6,241,747 B1 | 6/2001 | Ruff |
| 6,278,036 B1 | 8/2001 | Anhauser et al. |
| 6,287,316 B1 | 9/2001 | Agarwal et al. |
| 6,345,623 B1 | 2/2002 | Heaton et al. |
| 6,468,626 B1 | 10/2002 | Takai et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,623,681 B1 | 9/2003 | Taguchi et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |

(56) References Cited

U.S. PATENT DOCUMENTS

| | | | |
|---|---|---|---|
| 7,135,606 B1 * | 11/2006 | Dozier | A61F 13/0203 |
| | | | 602/56 |
| 7,195,624 B2 | 3/2007 | Lockwood et al. | |
| 7,338,482 B2 | 3/2008 | Lockwood et al. | |
| 7,381,859 B2 | 6/2008 | Hunt et al. | |
| 7,534,927 B2 | 5/2009 | Lockwood et al. | |
| 7,846,141 B2 | 12/2010 | Weston | |
| 7,867,206 B2 | 1/2011 | Lockwood et al. | |
| 7,880,050 B2 | 2/2011 | Robinson et al. | |
| 7,896,864 B2 | 3/2011 | Lockwood et al. | |
| 7,951,100 B2 | 5/2011 | Hunt et al. | |
| 7,988,680 B2 | 8/2011 | Lockwood et al. | |
| 8,062,273 B2 | 11/2011 | Weston | |
| 8,148,595 B2 | 4/2012 | Robinson et al. | |
| 8,168,848 B2 | 5/2012 | Lockwood et al. | |
| 8,187,210 B2 | 5/2012 | Hunt et al. | |
| 8,216,198 B2 | 7/2012 | Heagle et al. | |
| 8,246,592 B2 | 8/2012 | Lockwood et al. | |
| 8,251,979 B2 | 8/2012 | Malhi | |
| 8,257,327 B2 | 9/2012 | Blott et al. | |
| 8,350,116 B2 | 1/2013 | Lockwood et al. | |
| 8,398,614 B2 | 3/2013 | Blott et al. | |
| 8,449,509 B2 | 5/2013 | Weston | |
| 8,454,580 B2 * | 6/2013 | Locke | A61M 1/0023 |
| | | | 604/313 |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,672,903 B2 | 3/2014 | Hunt et al. | |
| 8,679,081 B2 | 3/2014 | Heagle et al. | |
| 8,680,359 B2 | 3/2014 | Robinson et al. | |
| 8,690,844 B2 | 4/2014 | Locke et al. | |
| 8,834,451 B2 | 9/2014 | Blott et al. | |
| 8,884,094 B2 | 11/2014 | Lockwood et al. | |
| 8,926,592 B2 | 1/2015 | Blott et al. | |
| 9,017,302 B2 | 4/2015 | Vitaris et al. | |
| 9,168,179 B2 | 10/2015 | Robinson et al. | |
| 9,198,801 B2 | 12/2015 | Weston | |
| 9,198,802 B2 | 12/2015 | Robinson et al. | |
| 9,211,365 B2 | 12/2015 | Weston | |
| 9,289,542 B2 | 3/2016 | Blott et al. | |
| 9,352,075 B2 | 5/2016 | Robinson et al. | |
| 9,445,947 B2 | 9/2016 | Hunt et al. | |
| 9,526,660 B2 | 12/2016 | Robinson et al. | |
| 9,844,471 B2 | 12/2017 | Lockwood et al. | |
| 10,016,544 B2 | 7/2018 | Coulthard et al. | |
| 10,045,886 B2 | 8/2018 | Lockwood et al. | |
| 2001/0043943 A1 | 11/2001 | Coffey | |
| 2002/0077661 A1 | 6/2002 | Saadat | |
| 2002/0082567 A1 | 6/2002 | Lockwood et al. | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0203011 A1 | 10/2003 | Abuelyaman et al. | |
| 2004/0030304 A1 * | 2/2004 | Hunt | A61F 13/00042 |
| | | | 604/317 |
| 2004/0126413 A1 | 7/2004 | Sigurjonsson et al. | |
| 2004/0138604 A1 | 7/2004 | Sigurjonsson et al. | |
| 2004/0148756 A1 | 8/2004 | Pommer | |
| 2004/0261295 A1 | 12/2004 | Meschter | |
| 2005/0226917 A1 | 10/2005 | Burton | |
| 2006/0241542 A1 | 10/2006 | Gudnason et al. | |
| 2007/0038172 A1 | 2/2007 | Zamierowski | |
| 2007/0185426 A1 | 8/2007 | Ambrosio et al. | |
| 2008/0300555 A1 | 12/2008 | Olson et al. | |
| 2009/0047495 A1 | 2/2009 | Hubbs | |
| 2009/0082746 A1 * | 3/2009 | Thomas | A61F 13/5146 |
| | | | 604/378 |
| 2009/0221979 A1 | 9/2009 | Huang et al. | |
| 2009/0234307 A1 | 9/2009 | Vitaris | |
| 2009/0293887 A1 | 12/2009 | Wilkes et al. | |
| 2010/0030170 A1 | 2/2010 | Keller et al. | |
| 2010/0030178 A1 | 2/2010 | MacMeccan et al. | |
| 2010/0036334 A1 * | 2/2010 | Heagle | A61M 1/982 |
| | | | 604/319 |
| 2010/0063484 A1 | 3/2010 | Heagle | |
| 2010/0069863 A1 | 3/2010 | Olson | |
| 2010/0069885 A1 * | 3/2010 | Stevenson | A61M 27/002 |
| | | | 606/1 |
| 2010/0106115 A1 | 4/2010 | Hardman et al. | |
| 2010/0159192 A1 | 6/2010 | Cotton | |
| 2010/0291184 A1 * | 11/2010 | Clark | A61L 15/18 |
| | | | 424/445 |
| 2010/0305490 A1 | 12/2010 | Coulthard et al. | |
| 2011/0054422 A1 | 3/2011 | Locke et al. | |
| 2011/0117178 A1 | 5/2011 | Junginger | |
| 2011/0160686 A1 | 6/2011 | Ueda et al. | |
| 2011/0178451 A1 * | 7/2011 | Robinson | A61F 13/00068 |
| | | | 264/237 |
| 2011/0213287 A1 * | 9/2011 | Lattimore | A61M 1/90 |
| | | | 604/319 |
| 2011/0224631 A1 | 9/2011 | Simmons et al. | |
| 2011/0282309 A1 | 11/2011 | Adie et al. | |
| 2011/0313374 A1 | 12/2011 | Lockwood et al. | |
| 2012/0046603 A1 | 2/2012 | Vinton | |
| 2012/0157945 A1 | 6/2012 | Robinson et al. | |
| 2012/0209226 A1 | 8/2012 | Simmons et al. | |
| 2012/0238932 A1 | 9/2012 | Atteia et al. | |
| 2013/0053748 A1 | 2/2013 | Cotton | |
| 2013/0152945 A1 | 6/2013 | Locke et al. | |
| 2013/0261534 A1 | 10/2013 | Niezgoda et al. | |
| 2014/0031771 A1 | 1/2014 | Locke et al. | |
| 2014/0052041 A1 | 2/2014 | Barberio | |
| 2014/0058309 A1 | 2/2014 | Addison et al. | |
| 2014/0081192 A1 | 3/2014 | Wenske et al. | |
| 2014/0094730 A1 | 4/2014 | Greener et al. | |
| 2014/0107562 A1 | 4/2014 | Dorian et al. | |
| 2014/0163447 A1 | 6/2014 | Wieland et al. | |
| 2014/0163491 A1 | 6/2014 | Schuessler et al. | |
| 2014/0188059 A1 | 7/2014 | Robinson et al. | |
| 2014/0200532 A1 | 7/2014 | Robinson et al. | |
| 2014/0228787 A1 | 8/2014 | Croizat et al. | |
| 2014/0236112 A1 | 8/2014 | Von Wolff et al. | |
| 2014/0350494 A1 | 11/2014 | Hartwell et al. | |
| 2014/0364819 A1 | 12/2014 | VanDelden | |
| 2015/0038933 A1 | 2/2015 | Day et al. | |
| 2015/0057624 A1 | 2/2015 | Simmons et al. | |
| 2015/0080788 A1 | 3/2015 | Blott et al. | |
| 2015/0119830 A1 | 4/2015 | Luckemeyer et al. | |
| 2015/0119831 A1 | 4/2015 | Robinson et al. | |
| 2015/0141941 A1 | 5/2015 | Allen et al. | |
| 2015/0150729 A1 | 6/2015 | Dagger et al. | |
| 2015/0174291 A1 | 6/2015 | Zimnitsky et al. | |
| 2015/0174304 A1 | 6/2015 | Askem et al. | |
| 2015/0290042 A1 | 10/2015 | Freer et al. | |
| 2015/0290050 A1 | 10/2015 | Wada | |
| 2015/0320434 A1 | 11/2015 | Ingram et al. | |
| 2015/0320602 A1 | 11/2015 | Locke et al. | |
| 2015/0320603 A1 | 11/2015 | Locke et al. | |
| 2016/0000610 A1 | 1/2016 | Riesinger | |
| 2016/0015571 A1 | 1/2016 | Robinson et al. | |
| 2016/0022885 A1 | 1/2016 | Dunn et al. | |
| 2016/0030646 A1 | 2/2016 | Hartwell et al. | |
| 2016/0095754 A1 | 4/2016 | Andrews et al. | |
| 2016/0144084 A1 | 5/2016 | Collinson et al. | |
| 2016/0144085 A1 | 5/2016 | Melin et al. | |
| 2016/0166744 A1 | 6/2016 | Hartwell | |
| 2016/0175156 A1 | 6/2016 | Locke et al. | |
| 2016/0199546 A1 * | 7/2016 | Chao | A61M 1/73 |
| | | | 604/318 |
| 2016/0199550 A1 | 7/2016 | Seddon et al. | |
| 2016/0220742 A1 | 8/2016 | Robinson et al. | |
| 2016/0262672 A1 | 9/2016 | Hammond et al. | |
| 2016/0354253 A1 | 12/2016 | Hunt et al. | |
| 2017/0014273 A1 | 1/2017 | Woodroof | |
| 2017/0079846 A1 | 3/2017 | Locke et al. | |
| 2017/0095374 A1 | 4/2017 | Lauer | |
| 2017/0172807 A1 | 6/2017 | Robinson et al. | |
| 2017/0174852 A1 | 6/2017 | Hanschen et al. | |
| 2017/0209312 A1 | 7/2017 | Kanchagar et al. | |
| 2017/0258640 A1 | 9/2017 | Ahsani Ghahreman et al. | |
| 2017/0312406 A1 | 11/2017 | Svensby | |

(56) References Cited

U.S. PATENT DOCUMENTS

| | | |
|---|---|---|
| 2017/0348154 A1 | 12/2017 | Robinson et al. |
| 2017/0348158 A1 | 12/2017 | You et al. |
| 2018/0071148 A1 | 3/2018 | Lockwood et al. |
| 2018/0289872 A1 | 10/2018 | Coulthard et al. |
| 2018/0296394 A1 | 10/2018 | Barberio |
| 2019/0184075 A1 | 6/2019 | Roos |
| 2021/0393443 A1* | 12/2021 | Steven .................... A61L 15/28 |

FOREIGN PATENT DOCUMENTS

| | | |
|---|---|---|
| AU | 755496 B2 | 12/2002 |
| CA | 2005436 A1 | 6/1990 |
| CN | 106390213 A | 2/2017 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0174803 A2 | 3/1986 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2468905 A | 9/2010 |
| JP | 2008073187 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 9319709 A1 | 10/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2007113597 A2 | 10/2007 |
| WO | 2009002260 A1 | 12/2008 |
| WO | 2010061228 A1 | 6/2010 |
| WO | 2011008497 A2 | 1/2011 |
| WO | 2011121127 A1 | 10/2011 |
| WO | 2011127188 A2 | 10/2011 |
| WO | 2011135286 A1 | 11/2011 |
| WO | 2012063725 A1 | 5/2012 |
| WO | 2014140608 A1 | 9/2014 |
| WO | 2015098373 A1 | 7/2015 |
| WO | 2015168681 A1 | 11/2015 |
| WO | 2015173547 A1 | 11/2015 |
| WO | 2015193257 A1 | 12/2015 |
| WO | 2016014645 A1 | 1/2016 |
| WO | 2016015001 A2 | 1/2016 |
| WO | 2017040045 A1 | 3/2017 |
| WO | 2017119996 A1 | 7/2017 |

OTHER PUBLICATIONS

3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Sided-Thermoplastic-Elastomer-TPE-Medical-Incise-Tape/?N=5002385+4294834151&rt=d; accessed May 21, 2019>.

International Search Report and Written Opinion for related application PCT/US2018/036013, dated Aug. 7, 2018.

International Search Report and Written Opinion for related application PCT/US2018/035945, dated Aug. 24, 2018.

International Search Report and Written Opinion for related application PCT/US2018/036074, dated Aug. 24, 2018.

International Search Report and Written Opinion for related application PCT/US2018/035957, dated Sep. 28, 2018.

International Search Report and Written Opinion for related application PCT/US2018/035995, dated Oct. 1, 2018.

International Search Report and Written Opinion for related application PCT/US2018/036021, dated Aug. 24, 2018.

International Search Report and Written Opinion for related application PCT/US2018/036019, dated Oct. 18, 2018.

International Search Report and Written Opinion for related application PCT/US2018/036054, dated Aug. 24, 2018.

International Search Report and Written Opinion for related application PCT/US2018/036049, dated Aug. 29, 2018.

International Search Report and Written Opinion for related application PCT/US2018/036077, dated Aug. 24, 2018.

International Search Report and Written Opinion for related application PCT/US2018/036129, dated Oct. 8, 2018.

Heit, et al., "Foam Pore Size Is a Critical Interface Parameter of Suction-Based Wound Healing Devices," copyright 2012 by the American Society of Plastic Surgeons (www.PRSJoumal.com) (Year: 2011).

Office Action for related U.S. Appl. No. 16/000,284, dated Sep. 23, 2019.

Office Action for related U.S. Appl. No. 16/000,284, dated Jun. 8, 2020.

Office Action for related U.S. Appl. No. 15/997,833, dated Jun. 19, 2020.

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

(56) References Cited

OTHER PUBLICATIONS

Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001, pp. 6646-6652.
Office Action for related U.S. Appl. No. 16/000,368, dated Dec. 14, 2020.
Office Action for related U.S. Appl. No. 15/997,809, dated Aug. 5, 2020.
Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Office Action for related U.S. Appl. No. 15/997,818, dated Jan. 27, 2021.
Office Action for related U.S. Appl. No. 15/997,841, dated Jan. 27, 2021.
Office Action for related U.S. Appl. No. 15/997,809, dated Jan. 28, 2021.
Office Action for related U.S. Appl. No. 15/997,833, dated Mar. 26, 2021.
Office Action for related U.S. Appl. No. 16/000,215, dated Apr. 12, 2021.
Chinese Office Action for related application 2018800367248, dated Apr. 28, 2021.
Office Action for related U.S. Appl. No. 15/997,833, dated Jun. 7, 2021.
Office Action for related U.S. Appl. No. 15/997,841, dated Jun. 8, 2021.
Chinese Office Action for related application 201880048393X, dated May 26, 2021.
Office Action for related U.S. Appl. No. 15/997,809, dated Jul. 8, 2021.
Chinese Office Action for related application 2018800436430, dated Jun. 8, 2021.
Office Action for related U.S. Appl. No. 15/997,818, dated Aug. 10, 2021.

(56) References Cited

OTHER PUBLICATIONS

Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.
Office action for related U.S. Appl. No. 16/000,002, dated Oct. 4, 2021.
Office Action for related U.S. Appl. No. 16/000,411, dated Jan. 31, 2022.
Office Action for related U.S. Appl. No. 16/959,651, dated Feb. 15, 2022.
Japanese Office Action for related application 2019-566886, dated Mar. 29, 2022.
Office Action for related U.S. Appl. No. 16/000,383, dated Mar. 31, 2022.
Pappas et al, "Wettability Tests of Polymer Films and Fabrics and Determination of Their Surface Energy by Contact-Angle Methods," Army Research Laboratory, ARL-TR-4056, Mar. 2007, p. 5.
Baltex, Technical Fabrics & Technical Textile Products, https://www.baltex.co.uk/products/xd-spacer-fabrics/, accessed Apr. 20, 2022.
Yimin Qin, Applications of Advanced Technologies in the Development of Functional Medical Textile Materials, Medical Textile Materials, 2016, pp. 55-70, Woodhead Publishing.
Baltex, Technical Fabrics & Technical Textile Products http://web.archive.org/web/20150118084138/http://www.baltex.co.uk/products/Healthcarefabrics/, 2015.
Office Action for related U.S. Appl. No. 17/204,548, dated Apr. 19, 2022.
Office Action for related U.S. Appl. No. 15/997,818, dated Jun. 9, 2022.
Japanese Office Action for related application 2019-567267, dated Jun. 7, 2022.
Japanese Office Action for related application 2019-566969, dated Jun. 7, 2022.
Japanese Office Action for related application 2019-567266, dated Jun. 7, 2022.
Japanese Office Action for related application 2019-566908, dated Aug. 2, 2022.

* cited by examiner

SYSTEMS, APPARATUSES, AND METHODS FOR NEGATIVE-PRESSURE TREATMENT WITH REDUCED TISSUE IN-GROWTH

RELATED APPLICATION

This application claims the benefit, under 35 U.S.C. § 119(e), of the filing of U.S. Provisional Patent Application Ser. No. 62/576,498, entitled "SYSTEMS, APPARATUSES, AND METHODS FOR NEGATIVE-PRESSURE TREATMENT WITH REDUCED TISSUE IN-GROWTH," filed Oct. 24, 2017; U.S. Provisional Patent Application Ser. No. 62/565,754, entitled "COMPOSITE DRESSINGS FOR IMPROVED GRANULATION AND REDUCED MACERATION WITH NEGATIVE-PRESSURE TREATMENT," filed Sep. 29, 2017; U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017, each of which is incorporated herein by reference for all purposes.

TECHNICAL FIELD

The invention set forth in the appended claims relates generally to tissue treatment systems and more particularly, but without limitation, to systems, dressings, and fillers for negative-pressure tissue treatment, and methods of using systems, dressings, and fillers for negative-pressure tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing or filler for treating a tissue site with negative-pressure may include a thin sheet of reticulated foam enclosed within at least two layers of perforated or fenestrated film. Suitable films may include, for example, polythene, polyurethane, or ethyl methyl acrylate. Some embodiments of the film may have linear perforations or fenestrations formed over the surface. The foam may be formed in sections in some embodiments. For example, the foam sections may be formed by joining the film layer around the sections. Sections may be formed in tessellating shapes in some examples, and the composite of foam and film may resemble a quilted structure in some configurations. Sections may be folded, cut, or otherwise separated to shape and size the dressing or filler for optimal placement, and exposure of the foam may be avoided or minimized by folding or separating the sections along joined film layers between sections.

More generally, in some embodiments, a dressing or filler for treating a tissue site with negative pressure may include a manifold having a first surface and a second surface opposite the first surface. The dressing may also include a first layer adjacent to the first surface and a second layer adjacent to the second surface. The first layer and the second layer may each include or consist of a polymer film in some embodiments. The dressing can also include a plurality of fluid restrictions in the polymer film adjacent to at least the first surface, and a plurality of bonds between the first layer and the second layer. The plurality of bonds generally defines separable sections of the manifold.

In some embodiments, the plurality of bonds form seams between the separable sections of the manifold. The seams between the sections generally have a width of at least 2 millimeters. The manifold may also include perforations, which may be aligned with the bonds in some examples. The manifold may additionally include sacrificial joints or bonds between the separable sections in some embodiments.

Some embodiments of a dressing may include a manifold having a first surface and a second surface opposite the first surface, a first layer adjacent to the first surface and a second layer adjacent to the second surface, the first layer and the second layer each including a polymer film, a plurality of fluid restrictions in the polymer film adjacent to at least the first surface, and a means for bonding the first layer to the second layer to form separable sections of the manifold.

A dressing may include at least two layers of manifold sections in some examples. At least one intermediate layer may be disposed between the first manifold layer and the second manifold layer. Some embodiments of the dressing may additionally include a first outer layer adjacent to the first manifold layer opposite the intermediate layer, a second outer layer adjacent to the second manifold layer opposite the intermediate layer, a plurality of fluid restrictions in the first outer layer and the second outer layer, and a plurality of bonds between the first outer layer and the intermediate layer and between the second outer layer and the intermediate layer. At least the first outer layer and the second outer layer may each comprise a polymer film. The plurality of bonds can define separable sections of the first manifold layer and the second manifold layer.

Other embodiments may relate to an apparatus for providing negative-pressure treatment to a tissue site. For example, an apparatus may include a manifold comprising a first surface and a second surface opposite the first surface, a first layer adjacent to the first surface and a second layer adjacent to the second surface, the first layer and the second layer each comprising a polymer film, a plurality of fluid restrictions in the polymer film adjacent to at least the first surface, a plurality of bonds between the first layer and the second layer, the plurality of bonds defining separable sections of the manifold, and a negative-pressure source fluidly coupled to the manifold.

Other example embodiments may relate to a method for treating a tissue site. Some methods may include excising separable sections of a dressing based upon at least one of a size and shape of a tissue site, applying the dressing to fill or cover the tissue site, sealing the dressing to epidermis adjacent to the tissue site, fluidly coupling the dressing to a negative-pressure source, and applying negative pressure from the negative-pressure source to the dressing.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
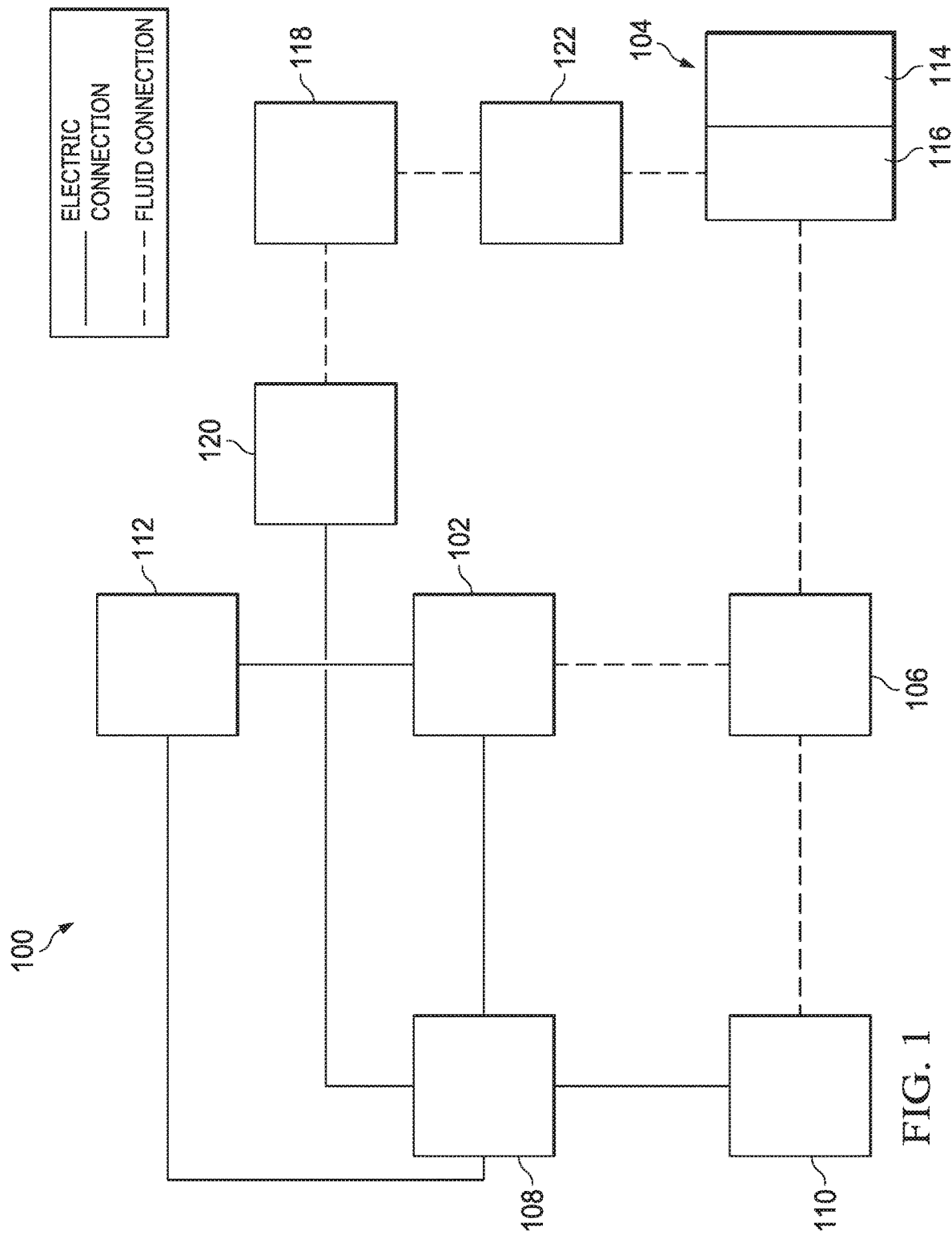
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of a tissue interface 114, a cover 116, or both in some embodiments.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an installation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108, and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108, and may be fluidly coupled to one or more distribution components to provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of 14400 g/m²/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, Calif.; polyether block polyamide copolymer (PEBAX), for example, from Arkema, France; INSPIRE 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
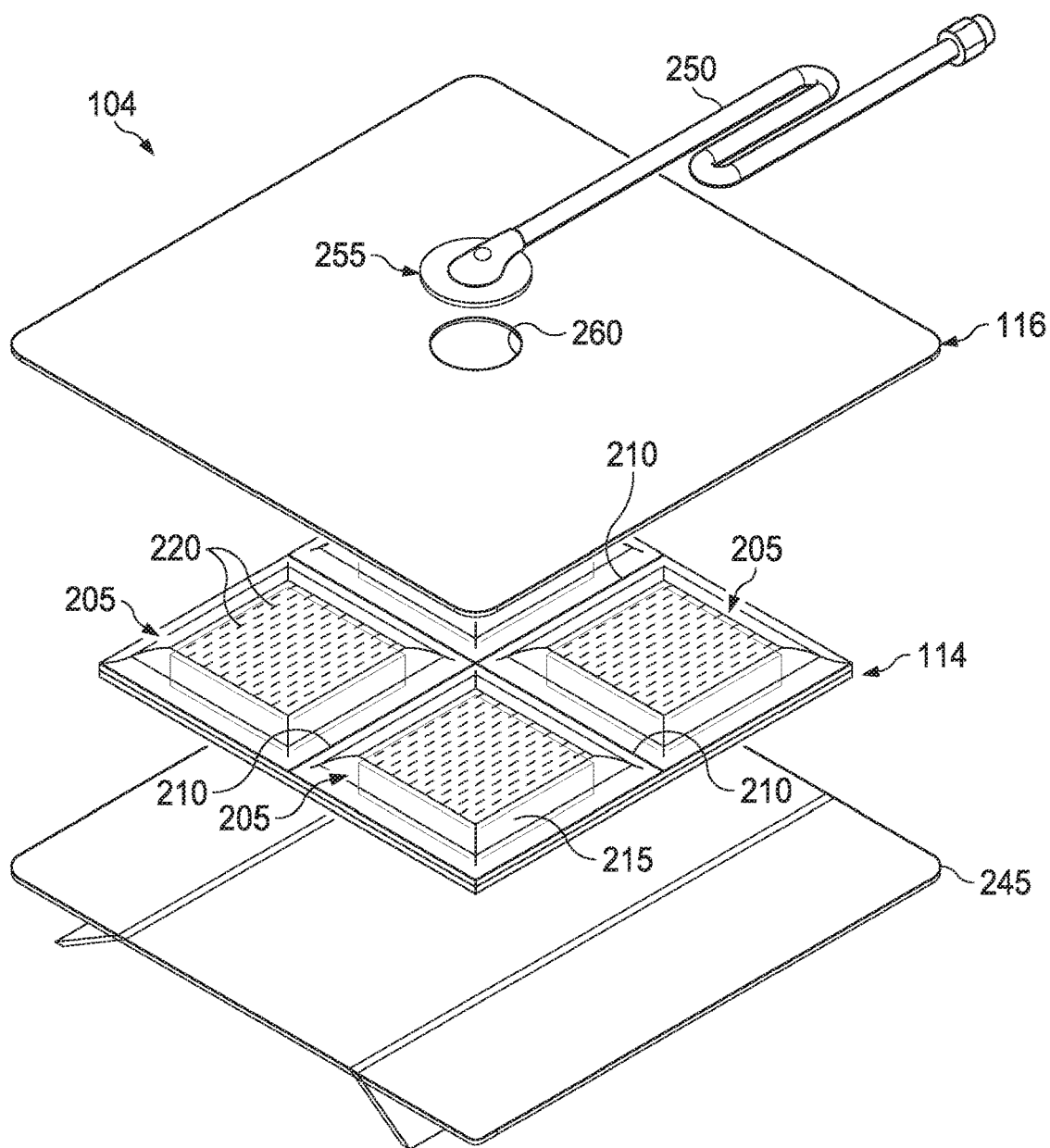
FIG. 2 is an exploded view of a dressing that may be associated with an example embodiment of the therapy system of FIG. 1.

FIG. 2 is an assembly view of an example of the dressing 104 of FIG. 1, illustrating additional details that may be associated with some embodiments in which the tissue interface 114 comprises separable sections. In the example of FIG. 2, the tissue interface 114 comprises one or more interface sections 205, which may be bounded by seams 210. Each of the interface sections 205 may include a manifold section 215. In some examples, seams 210 may be formed between or may define the manifold sections 215.

The manifold sections 215 may comprise or consist of foam in some embodiments. For example, the foam may be open-cell foam, such as reticulated foam. The foam may also be relatively thin and hydrophobic to reduce the fluid hold capacity of the dressing, which can encourage exudate and other fluid to pass quickly to external storage. The foam layer may also be thin to reduce the dressing profile and increase flexibility, which can enable it to conform to wound beds and other tissue sites under negative pressure. In some embodiments, the manifold sections 215 may be formed of 3-dimensional textiles, non-woven wicking material, vacuum-formed texture surfaces, and composites thereof. A hydrophobic manifold having a thickness of less than 7 millimeters and a free volume of at least 90% may be suitable for many therapeutic applications. In some embodiments, the manifold sections 215 may be formed of colored material. Each of the manifold sections 215 may be a same color or a different color.

As illustrated in the example of FIG. 2, the tissue interface 114 may have one or more fluid restrictions 220, which can be distributed uniformly or randomly across the tissue interface 114. The fluid restrictions 220 may be bi-directional and pressure-responsive. For example, each of the fluid restrictions 220 generally may comprise or consist essentially of an elastic passage that is normally unstrained to substantially reduce liquid flow, and can expand or open in response to a pressure gradient. The fluid restrictions 220 may be coextensive with the manifold sections 215.

For example, some embodiments of the fluid restrictions 220 may comprise or consist essentially of one or more slits, slots or combinations of slits and slots. In some examples, the fluid restrictions 220 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. In some embodiments, the fluid restrictions 220 may be formed by ultrasonics or other heat means. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

As illustrated in the example of FIG. 2, in some embodiments, the dressing 104 may include a release liner 245 to protect an optional adhesive on a portion of the cover 116 prior to use. The release liner 245 may also provide stiffness to assist with, for example, deployment of the dressing 104. The release liner 245 may be, for example, a casting paper, a film, or polyethylene. Further, in some embodiments, the release liner 245 may be a polyester material such as polyethylene terephthalate (PET), or similar polar semi-crystalline polymer. The use of a polar semi-crystalline polymer for the release liner 245 may substantially preclude wrinkling or other deformation of the dressing 104. For example, the polar semi-crystalline polymer may be highly orientated and resistant to softening, swelling, or other deformation that may occur when brought into contact with components of the dressing 104, or when subjected to temperature or environmental variations, or sterilization. Further, a release agent may be disposed on a side of the release liner 245 that is configured to contact the tissue interface 114. For example, the release agent may be a silicone coating and may have a release factor suitable to facilitate removal of the release liner 245 by hand and without damaging or deforming the dressing 104. In some embodiments, the release agent may be a fluorocarbon or a fluorosilicone, for example. In other embodiments, the release liner 245 may be uncoated or otherwise used without a release agent.

FIG. 2 also illustrates one example of a fluid conductor 250 and a dressing interface 255. As shown in the example of FIG. 2, the fluid conductor 250 may be a flexible tube, which can be fluidly coupled on one end to the dressing interface 255. The dressing interface 255 may be an elbow connector, as shown in the example of FIG. 2, which can be placed over an aperture 260 in the cover 116 to provide a fluid path between the fluid conductor 250 and the tissue interface 114.

Figure 3:
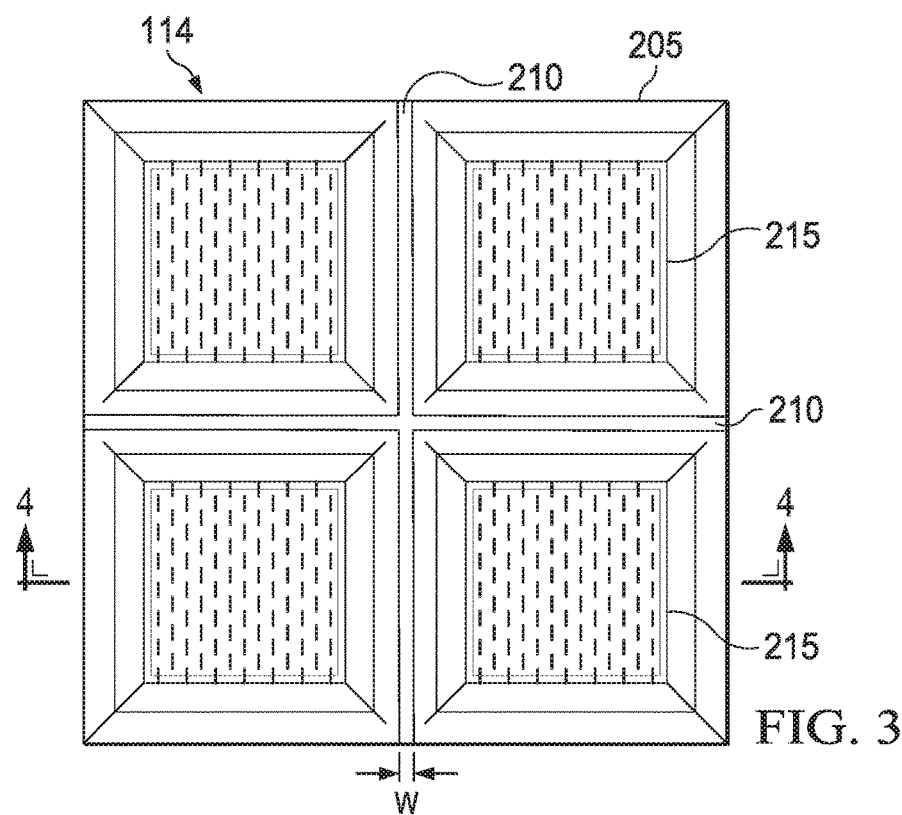
FIG. 3 is a top view of a manifold of the dressing of FIG. 2.

FIG. 3 is a top view of the tissue interface 114 of FIG. 2, illustrating additional details that may be associated with some examples. The manifold sections 215 in each of the interface sections 205 may have a same shape or a different shape. As shown in the example of FIG. 3, the interface sections 205 and the manifold sections 215 may have similar shapes. In some embodiments, each of the interface sections 205 and the manifold sections 215 may have a tessellate shape, such as the generally square shape in the example of FIG. 3, with sides having a length ranging from about 10 mm to about 30 mm (e.g., about 15 mm to about 25 mm or about 18 mm to about 22 mm). For example, the manifold sections 215 may be squares having dimensions of about 20 mm by about 20 mm.

Each of the seams 210 may have a width W ranging from about 2 mm to about 5 mm, and may be wide enough to allow for the interface sections 205 to be separated along the seams 210 without exposing any portion of the manifold sections 215.

Figure 4:
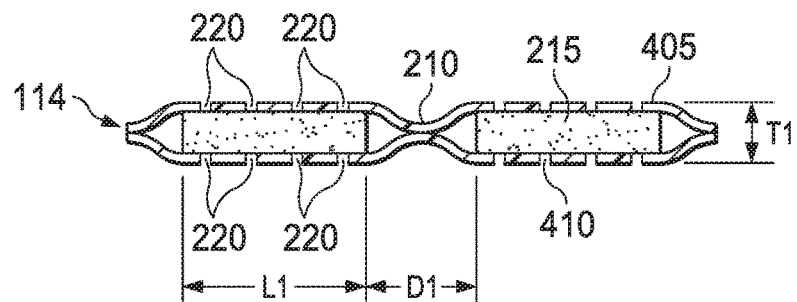
FIG. 4 is a cross-sectional view of the manifold of FIG. 3.

FIG. 4 is a section view of the tissue interface 114 of FIG. 3 taken along line 4-4, illustrating additional details that may be associated with some embodiments. In the example of FIG. 4, the tissue interface 114 comprises a first layer 405, a second layer 410, and the manifold sections 215 disposed between the first layer 405 and the second layer 410. In some embodiments, the first layer 405 and the second layer 410 may be disposed adjacent to the manifold sections 215 as shown in the example of FIG. 4. Also as shown in the example of FIG. 4, the seams 210 may be formed by one or more bonds between the first layer 405 and the second layer 410. The bonds may be continuous or discrete.

The first layer 405 and the second layer 410 may comprise or consist essentially of a means for controlling or managing fluid flow. In some embodiments, the first layer 405 and the second layer 410 may comprise or consist essentially of an elastomeric material that is impermeable to liquid. For example, the first layer 405 and the second layer 410 may comprise or consist essentially of a polymer film. The first layer 405 and the second layer 410 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the second layer may have a substantially flat surface, with height variations limited to 0.2 millimeters over a centimeter.

In some embodiments, the first layer 405 and the second layer 410 may comprise or consist essentially of a hydrophobic material. The hydrophobicity may vary, but may have a contact angle with water of at least ninety degrees in some embodiments. In some embodiments the hydrophobic material may have a contact angle with water of no more than 150 degrees. For example, in some embodiments, the contact angle may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the first layer 405, the second layer 410, or both may be further enhanced with a hydrophobic coating of other materials, such as silicones and fluorocarbons, either as coated from a liquid, or plasma coated.

The first layer 405 and the second layer 410 may also be suitable for bonding to other layers, including each other. For example, the first layer 405, the second layer 410, or both may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene. The first layer 405 and the second layer 410 may include hot melt films.

The area density of the first layer 405 and the second layer 410 may vary according to a prescribed therapy or application. In some embodiments, an area density of less than 40 grams per square meter may be suitable, and an area density of about 20-30 grams per square meter may be particularly advantageous for some applications.

In some embodiments, for example, the first layer 405, the second layer 410, or both may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. Films may be clear, colored, or printed. More polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

In some embodiments, the fluid restrictions 220 may comprise or consist essentially of perforations in at least one of the first layer 405 and the second layer 410. Perforations may be formed by removing material from the first layer 405, the second layer 410, or both. For example, perforations may be formed by cutting through the material, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fluid restrictions 220 may be an elastomeric valve that is normally closed when unstrained to substantially prevent liquid flow, and can open in response to a pressure gradient. A fenestration in the material may be a suitable valve for some applications. Fenestrations may also be formed by removing material, but the amount of material removed and the resulting dimensions of the fenestrations may be an order of magnitude less than perforations, and may not deform the edges. In some embodiments, the fluid restrictions 220 extend through both the first layer 405 and the second layer 410, and the fluid restrictions 220 are coextensive with at least one of the first layer 405 and the second layer 410.

Each of the manifold sections 215 has a length L1, which can be in a range from about 10 mm to about 30 mm (e.g., about 15 mm to about 25 mm or about 18 mm to about 22 mm). For example, each of the manifold sections 215 may have a length of about 20 mm. In some embodiments, the manifold sections 215 may be spaced apart by a distance D1 of about 5 mm to about 15 mm. For example, a distance D1 of about 10 mm may be particularly advantageous for some embodiments.

In some embodiments, each of the manifold sections 215 in the tissue interface 114 may be the same size. In other embodiments, one or more of the manifold sections 215 in the tissue interface 114 may have a different size.

In some embodiments, the tissue interface 114 has a thickness T1 ranging from about 5 mm to about 20 mm (e.g., about 8 mm to about 18 mm, or about 10 mm to about 15 mm). For example, the tissue interface 114 may have a thickness T1 of about 8 mm. The thickness T1 of the tissue interface 114 may vary depending upon a thickness of the manifold sections 215 used to form the tissue interface 114. For example, each of the manifold sections 215 may have a thickness ranging from about 5 mm to about 15 mm (e.g., about 8 mm to about 12 mm).

In some embodiments, the first layer 405 and the second layer 410 may be formed of a transparent polymer to aid in cutting the interface sections 205 apart along the seams 210.

In some embodiments, the tissue interface 114 can be formed by spacing the manifold sections 215 apart, placing the first layer 405 of polymer film over the manifold sections 215, placing the second layer 410 under the manifold sections 215, and bonding the first layer 405 to the second layer 410, forming the seams 210 between the manifold sections 215. Suitable means for bonding the first layer 405 to the second layer 410 may include, for example, an adhesive such as an acrylic, and welding, such as heat, radio frequency (RF), or ultrasonic welding. In some embodiments, sacrificial materials may be disposed between the first layer 405 and the second layer 410 to facilitate welding. Suitable sacrificial materials may include, for example, hot melt films supplied by Bayer (such as H2, HU2, and H5 films), Cornelius (Collano film), or Prochimir (such as TC203 or TC206 film).

In some embodiments, the manifold sections may be formed from an integral manifold material, such as foam. In some embodiments, for example, bonds between the first layer 405 and the second layer 410 may extend through a layer of manifold material to define the manifold sections 215. For example, some embodiments of a manifold layer may have a thickness ranging from about 5 mm to about 8 mm, and at least one of the first layer 405 and the second layer 410 may melt through the manifold layer during welding to form the seams 210.

Additionally or alternatively, a unitary manifold material can be perforated and cut to define the manifold sections 215 in a variety of suitable shapes and patterns. In some embodiments, the seams 210 may align with perforations between the manifold sections 215. In some examples, sacrificial joints may be left between the manifold sections 215 to maintain the manifold sections 215 together as a single unit. Maintaining the manifold sections 215 as a single unit can allow for easier assembly of the tissue interface 114. In some embodiments, either or both of the first layer 405 and the second layer 410 may also be bonded to the manifold sections 215 for additional stability.

Figure 5:
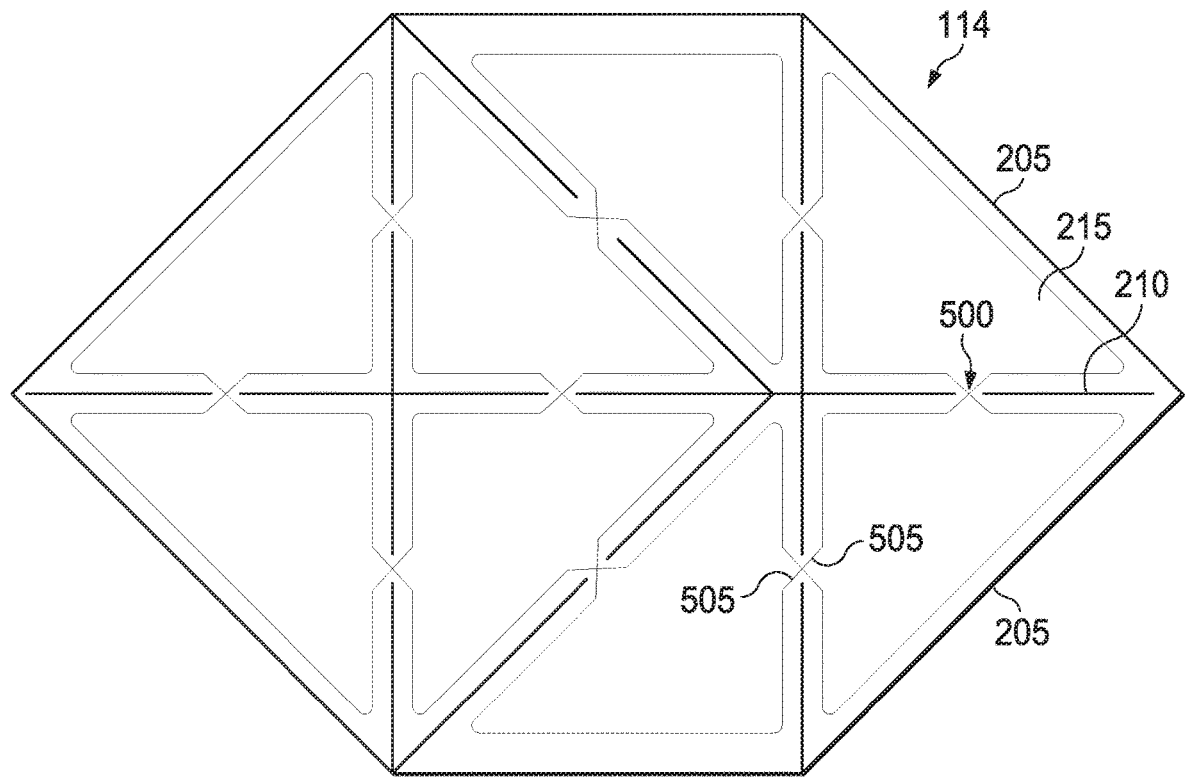
FIG. 5 is top view of a manifold of the dressing of FIG. 2.

FIG. 5 is a top view of another example of the tissue interface 114, illustrating additional details that may be associated with some embodiments. In the example of FIG. 5, the interface sections 205 have generally triangular shapes. In some embodiments, the manifold sections 215 within the interface sections 205 also have generally triangular shapes. The triangular shapes may be equilateral triangles, isosceles triangles, or scalene triangles, for example. One or more sacrificial joints 500 may couple the manifold sections 215 together in some embodiments. For example, in some embodiments a manifold material such as foam may be shaped and perforated to form the manifold sections 215, leaving the sacrificial joints 500 between the manifold sections 215. In the example of FIG. 5, the sacrificial joints 500 comprise extensions 505, which may have a generally triangular shape. The extensions 505 of FIG. 5 are joined at a common apex, which can minimize potential exposure of manifold material if the interface sections 205 are separated. The first layer 405 can be bonded to the second layer 410 around and/or through the extensions 505 so as to form the seams 210 between the interface sections 205.

In some example embodiments, the tissue interface 114 may have a generally hexagonal shape. One or more sides of the tissue interface 114 may have a same length or a different length.

The tissue interface 114 may include eight interface sections 205, as illustrated in the example of FIG. 5. In some embodiments, the tissue interface 114 may include one or more of the interface sections 205, depending on dimensions of each of the interface sections 205.

Figure 6:
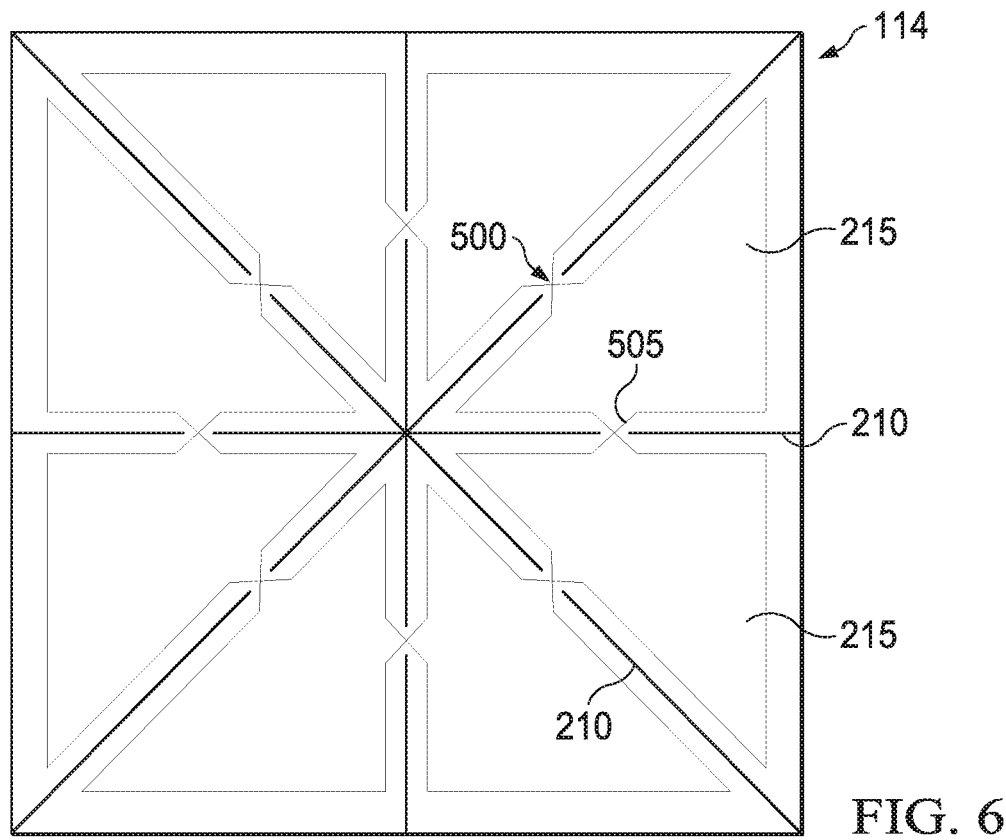
FIG. 6 is a top view of a manifold of the dressing of FIG. 2.

FIG. 6 is a top view of another example of the tissue interface 114, illustrating additional details that may be associated with some embodiments. In the example of FIG. 6, the tissue interface 114 has a generally square shape and each of the interface sections 205 in the tissue interface 114 has a generally triangular shape. The tissue interface 114 of FIG. 6 includes eight of the interface sections 205.

Figure 7:
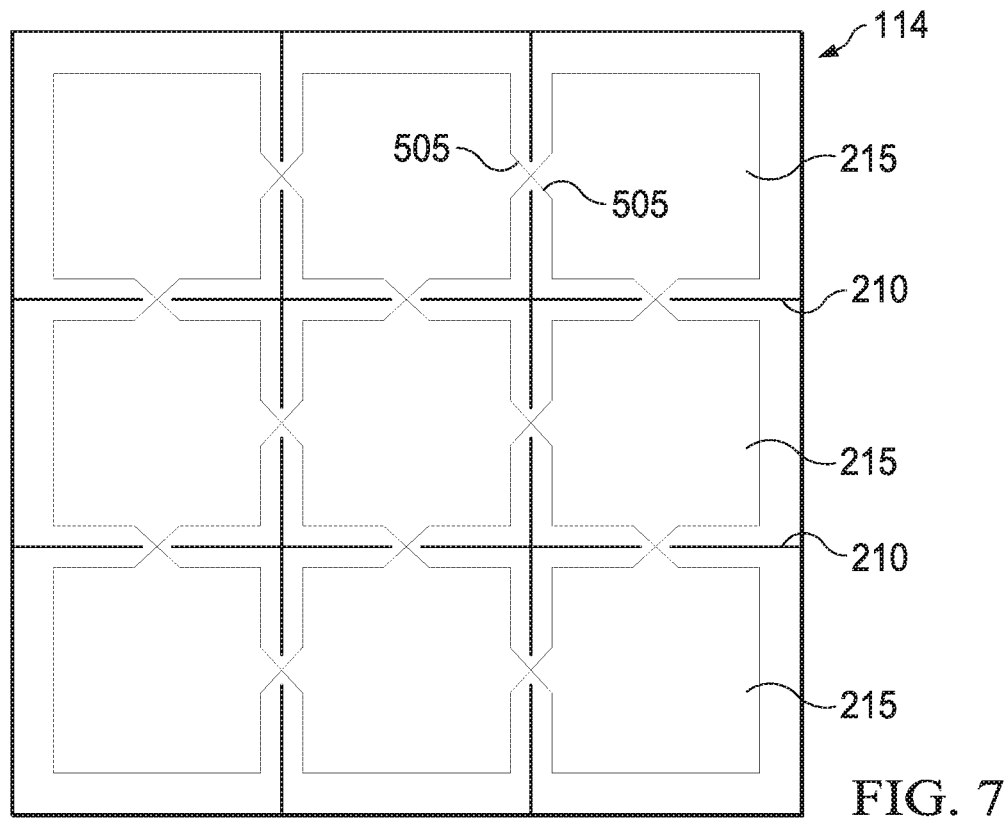
FIG. 7 is a top view of a manifold of the dressing of FIG. 2.

FIG. 7 is a top view of another example of the tissue interface 114, illustrating additional details that may be associated with some embodiments. In the example of FIG. 7, the interface sections 205 have generally square shapes. Each of the manifold sections 215 also has a generally square shape, and can be attached to adjacent manifold sections 215 by the sacrificial joints 500. The tissue interface 114 of FIG. 7 includes nine of the interface sections 205.

In other embodiments, the tissue interface 114 may include more or fewer of the interface sections 205. Each of the interface sections 205 may have a different size or a same size. Each of the interface sections 205 may have a same shape or a different shape. For example, the interface sections 205 may be in the form of equilateral polygons, which may have sides not exceeding about 20 millimeters and having an area less than about 400 square millimeters.

Figure 8:
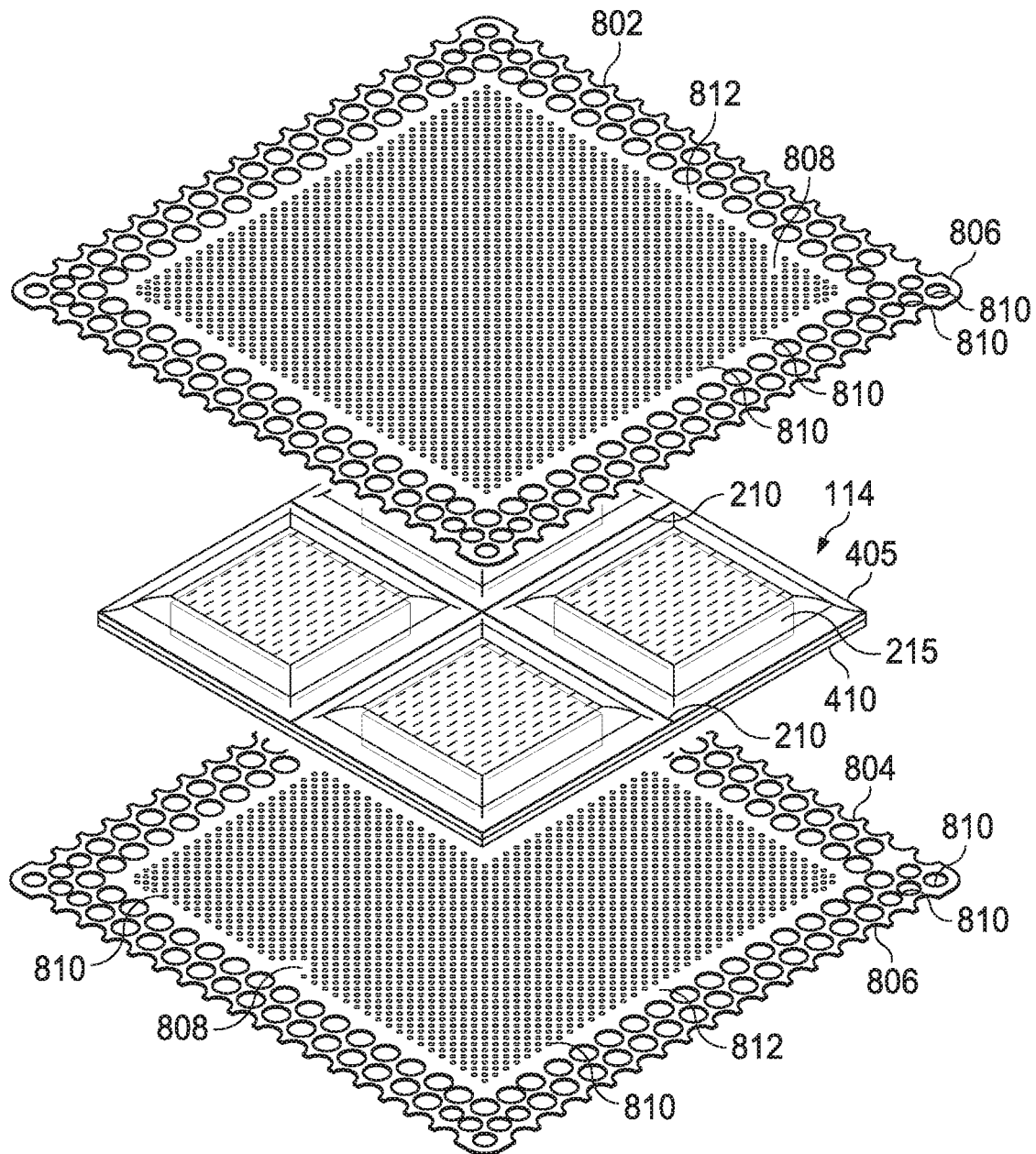
FIG. 8 is an exploded view of a manifold that may be associated with an example embodiment of a dressing of the therapy system of FIG. 1.

FIG. 8 is an assembly view of another example of the tissue interface 114 of FIG. 1. In the example of FIG. 8, the tissue interface 114 includes the first layer 405, the second layer 410, the manifold sections 215, a third layer 802, and a fourth layer 804.

The third layer 802, the fourth layer 804, or both may comprise or consist essentially of a soft, pliable material suitable for providing a fluid seal with a tissue site, and may have a substantially flat surface. The third layer 802, the fourth layer 804, or both may be a sealing layer. In some embodiments, the third layer 802, the fourth layer 804, or both may also be adhesive. For example, the third layer 802 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. A silicone gel having a coating weight of about 100 g.s.m. to about 150 g.s.m. may be suitable for some applications. In some embodiments, the third layer 802, the fourth layer 804, or both may have a thickness between about 200 microns ($\mu$m) and about 1000 microns ($\mu$m). In some embodiments, the third layer 802, the fourth layer 804, or both may have a hardness between about 5 Shore OO and about 80 Shore OO. Further, the third layer 802, the fourth layer 804, or both may be comprised of hydrophobic or hydrophilic materials.

In some embodiments, the third layer 802, the fourth layer 804, or both may be a hydrophobic-coated material. For example, either or both may be formed by coating a spaced material, such as, for example, woven, nonwoven, molded, or extruded mesh with a hydrophobic material. The hydrophobic material for the coating may be a soft silicone, for example.

The third layer 802, the fourth layer 804, or both may have a periphery 806 surrounding or around an interior portion 808, and apertures 810 disposed through the periphery 806 and/or the interior portion 808. The interior portion 808 may correspond to a surface area of the first layer 405 or the second layer 410 in some examples. An interior border 812 may be disposed around the interior portion 808, between the interior portion 808 and the periphery 806. The interior border 812 may be substantially free of the apertures 810, as illustrated in the example of FIG. 8. In some examples, as illustrated in FIG. 8, the interior portion 808 may be symmetrical and centrally disposed.

The apertures 810 may be formed by cutting or by application of local RF or ultrasonic energy, for example, or by other suitable techniques for forming an opening. The apertures 810 may have a uniform distribution pattern, or may be randomly distributed on the third layer 802, the fourth layer 804, or both. The apertures 810 may have many shapes, including circles, squares, stars, ovals, polygons, slits, complex curves, rectilinear shapes, triangles, for example, or may have some combination of such shapes.

Each of the apertures 810 may have uniform or similar geometric properties. For example, in some embodiments, each of the apertures 810 may be circular apertures, having substantially the same diameter. In some embodiments, the diameter of each of the apertures 810 may range from about 1 millimeter to about 50 millimeters. In other embodiments, the diameter of each of the apertures 810 may range from about 1 millimeter to about 20 millimeters.

In other embodiments, geometric properties of the apertures 810 may vary. For example, the diameter of the apertures 810 may vary depending on the position of the apertures 810. In some embodiments, the diameter of the apertures 810 in the periphery 806 may be larger than the diameter of the apertures 810 in the interior portion 808. For example, in some embodiments, the apertures 810 disposed in the periphery 806 may have a diameter ranging from about 9.8 millimeters to about 10.2 millimeters. In some embodiments, the apertures 810 disposed in the corners may have a diameter ranging from about 7.75 millimeters to about 8.75 millimeters. In some embodiments, the apertures 810 disposed in the interior portion 808 may have a diameter ranging from about 1.8 millimeters to about 2.2 millimeters.

At least one of the apertures 810 in the periphery 806 may be positioned at an edge of the periphery 806, and may have an interior cut open or exposed at the edge that is in fluid communication in a lateral direction with the edge. As shown in the example of FIG. 8, the apertures 810 in the periphery 806 may be positioned proximate to or at the edges and in fluid communication in a lateral direction with the edges. The apertures 810 positioned proximate to or at the edges may be spaced substantially equidistant around the periphery 806 as shown in the example of FIG. 8. Alternatively, the spacing of the apertures 810 proximate to or at the edges may be irregular.

Figure 9:
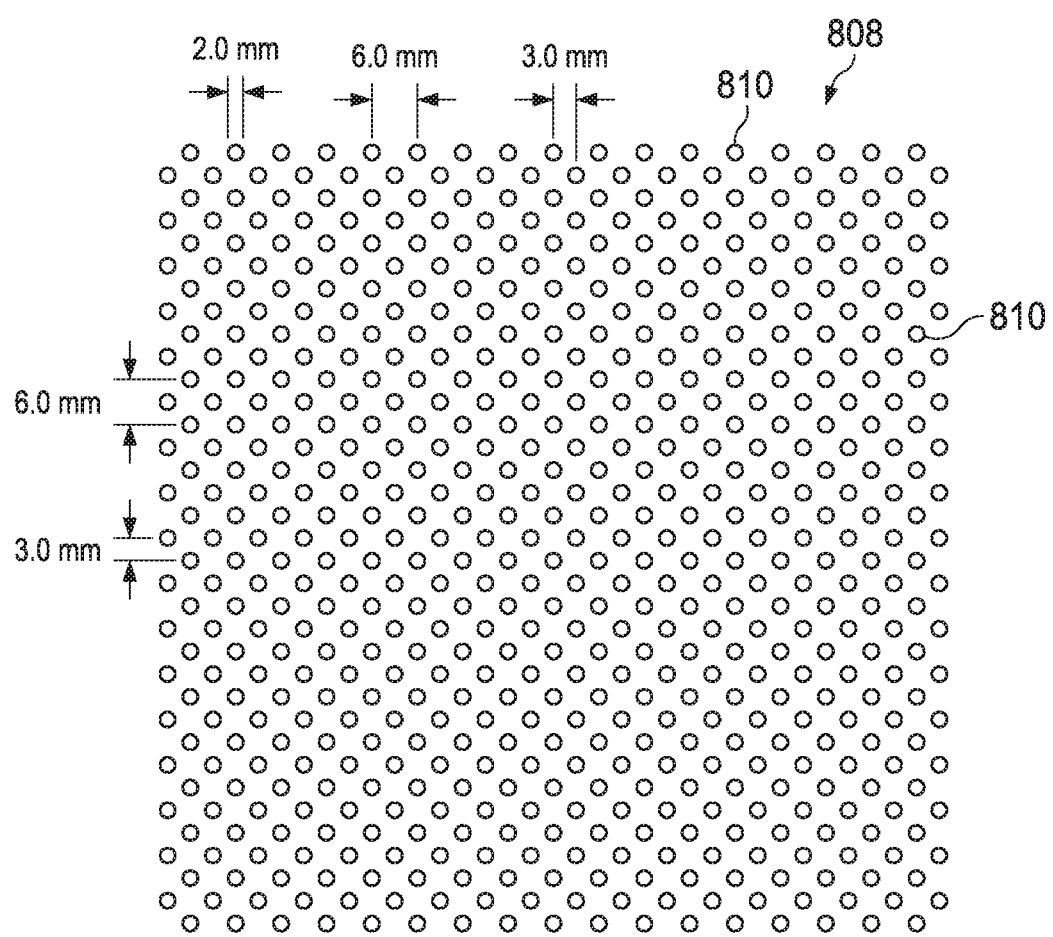
FIG. 9 is a schematic view of an example configuration of fluid restrictions in a layer that may be associated with some embodiments of the dressing of FIG. 2.

FIG. 9 is a schematic view of an example configuration of the apertures 810, illustrating additional details that may be associated with some embodiments of the third layer 802, the fourth layer 804, or both.

In some embodiments, the apertures 810 may be arranged in rows, columns, or a grid of rows and columns. The apertures 810 may be offset in some embodiments. For example, as illustrated in FIG. 9, the apertures 810 in one row may be offset from the apertures 810 in adjacent rows, and the apertures in one column may be offset from the apertures in adjacent columns. In other embodiments, the apertures 810 in adjacent rows or columns may be aligned. A pattern of the apertures 810 may be substantially uniform in some configurations. Within each row and column, for example, the apertures 810 may be equidistant from each other. FIG. 9 illustrates one example configuration that may be particularly suitable for many applications, in which the apertures 810 are spaced about 6 millimeters apart along each row and column, with a 3 millimeter offset. The apertures 810 in the interior portion 808 of FIG. 9 have a diameter of about 2.0 mm. In some embodiments, the pattern of apertures 810 is non-uniform.

Figure 10:
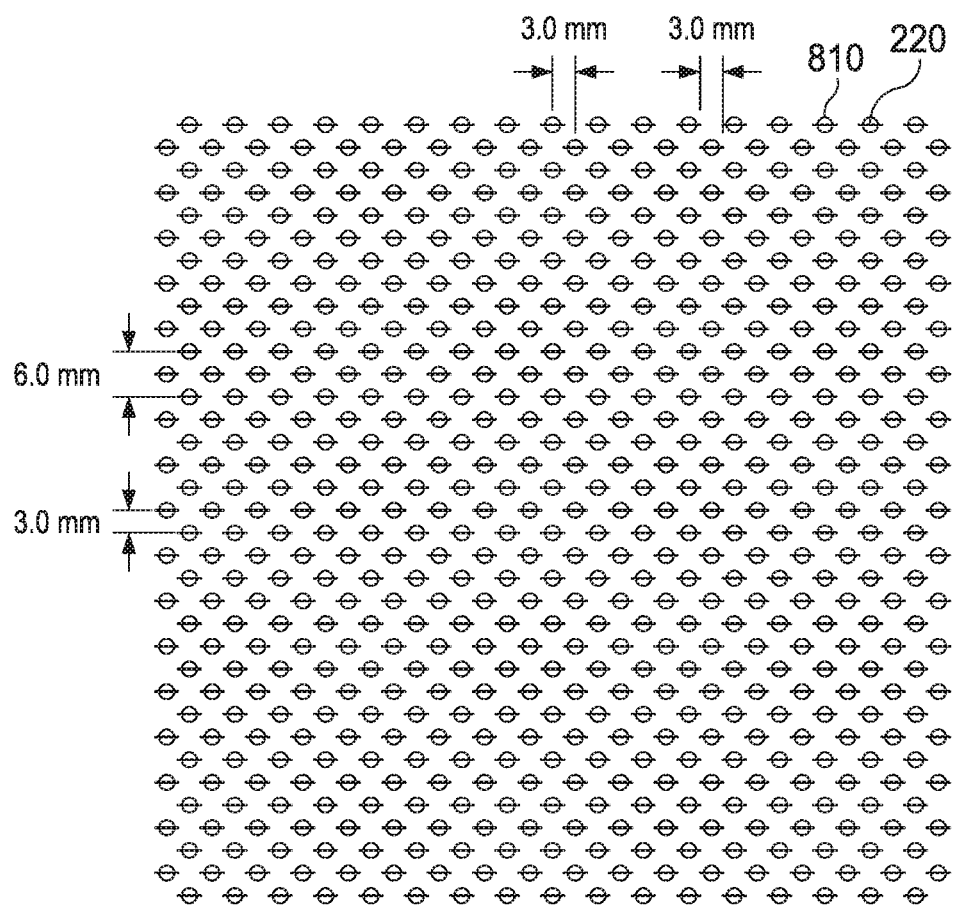
FIG. 10 is a schematic view of the example layer of FIG. 9 overlaid on the example layer of FIG. 3.

FIG. 10 is a schematic view of the example configuration of the apertures 810 of FIG. 9 overlaid on an example configuration of the fluid restrictions 220, illustrating additional details that may be associated with some example embodiments of the tissue interface 114. For example, as illustrated in FIG. 10, the fluid restrictions 220 may be aligned, overlapping, in registration with, or otherwise fluidly coupled to at least some of the apertures 810 in some embodiments. In some embodiments, one or more of the fluid restrictions 220 may be registered with the apertures 810 only in the interior portion 808, or only partially registered with the apertures 810. The fluid restrictions 220 in the example of FIG. 10 are generally configured so that each of the fluid restrictions 220 is registered with only one of the apertures 810. In other examples, one or more of the fluid restrictions 220 may be registered with more than one of the apertures 810. For example, any one or more of the fluid restrictions 220 may be a perforation or a fenestration that extends across two or more of the apertures 810. Additionally or alternatively, one or more of the fluid restrictions 220 may not be registered with any of the apertures 810.

Figure 11:
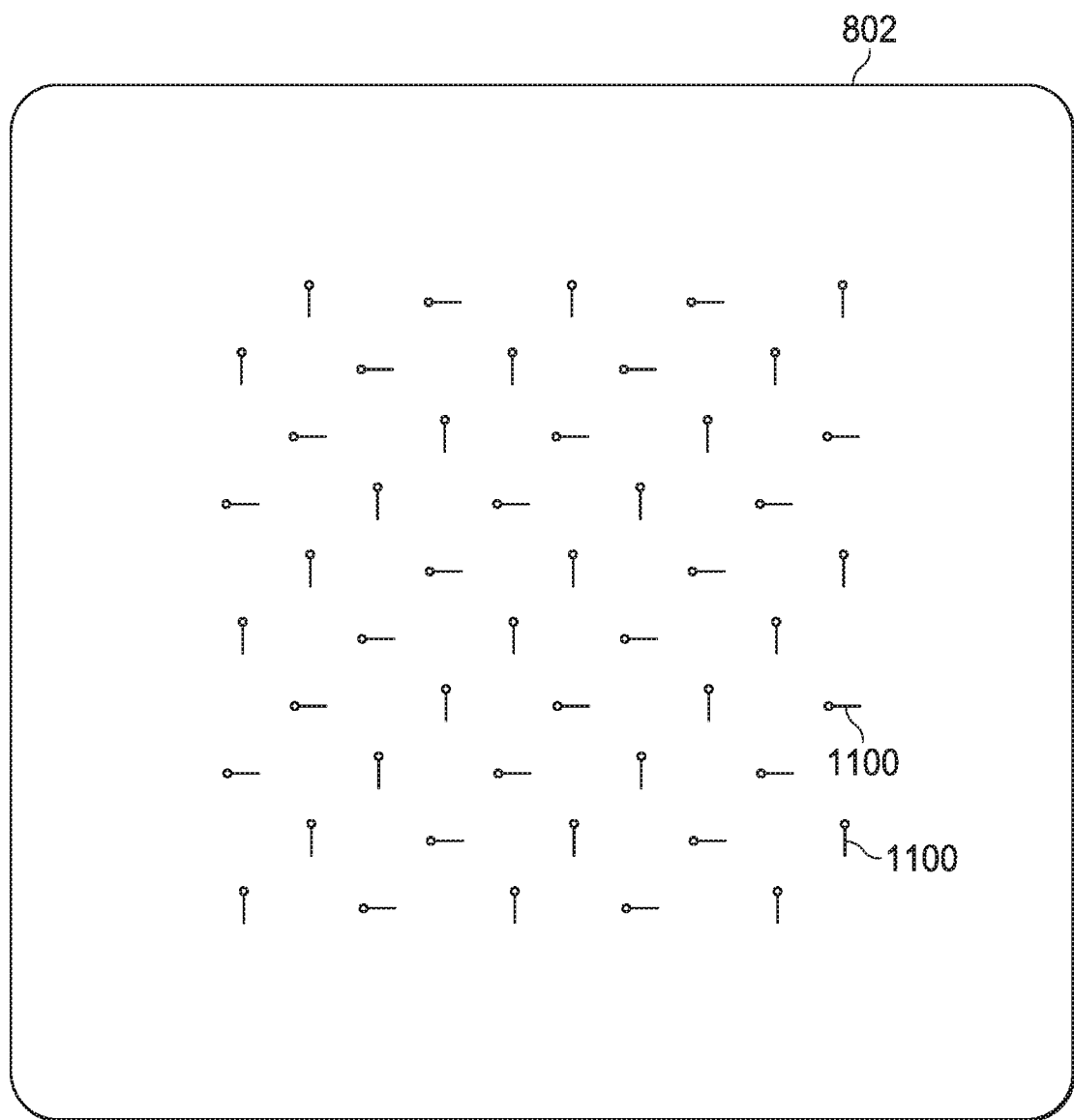
FIG. 11 is a schematic view of another example of another dressing layer, illustrating additional details that may be associated with some embodiments.

FIG. 11 is a schematic view of another example of the third layer 802, illustrating additional details that may be associated with some embodiments. As shown in the example of FIG. 11, the third layer 802 may have one or more fluid restrictions, such as valves 1100, instead of or in addition to the apertures 810 in the interior portion 808. The valves 1100 may be elastomeric.

Figure 12:
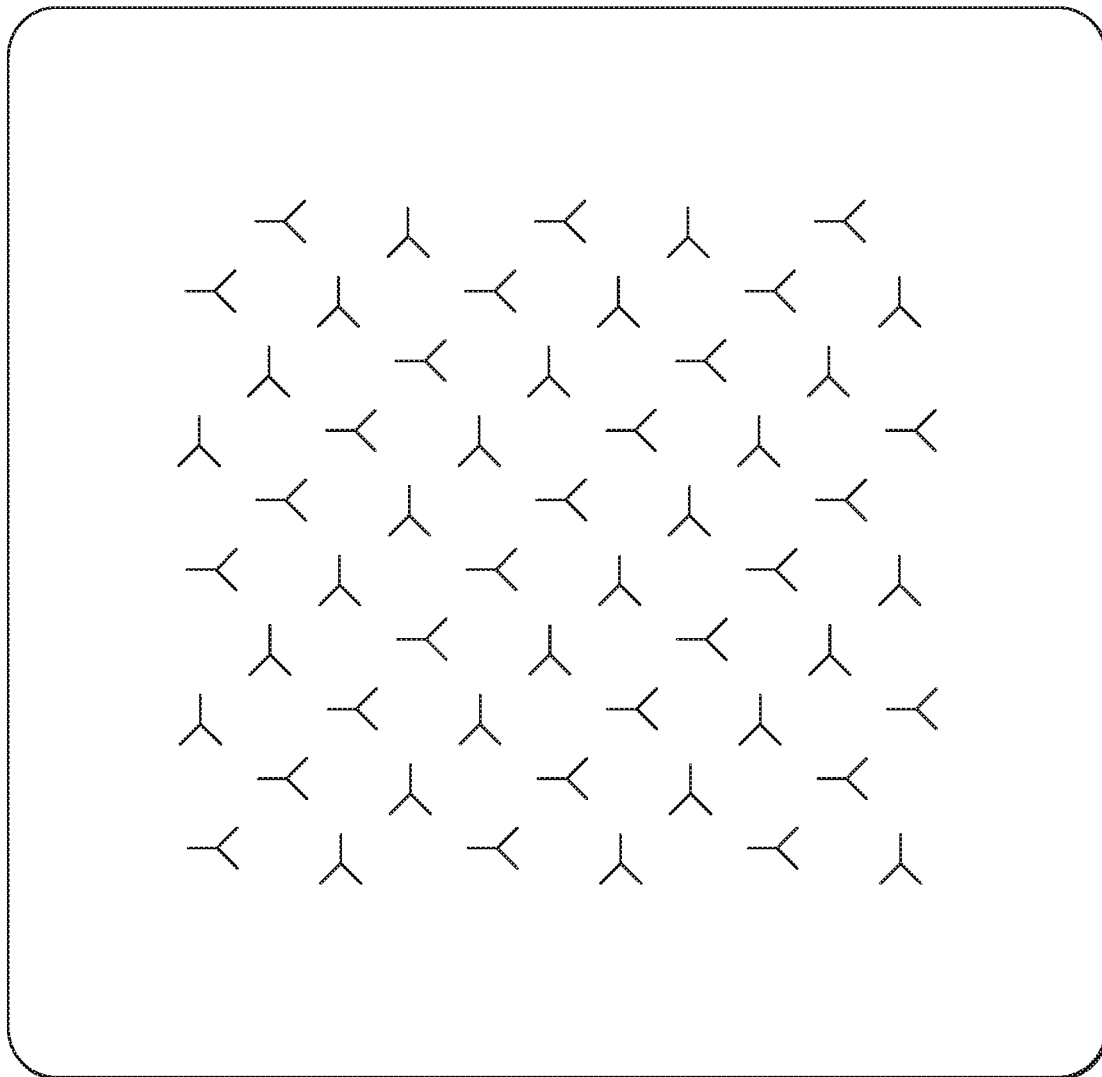
FIG. 12 is a schematic view of another example of another dressing layer, illustrating additional details that may be associated with some embodiments.
Figure 13:
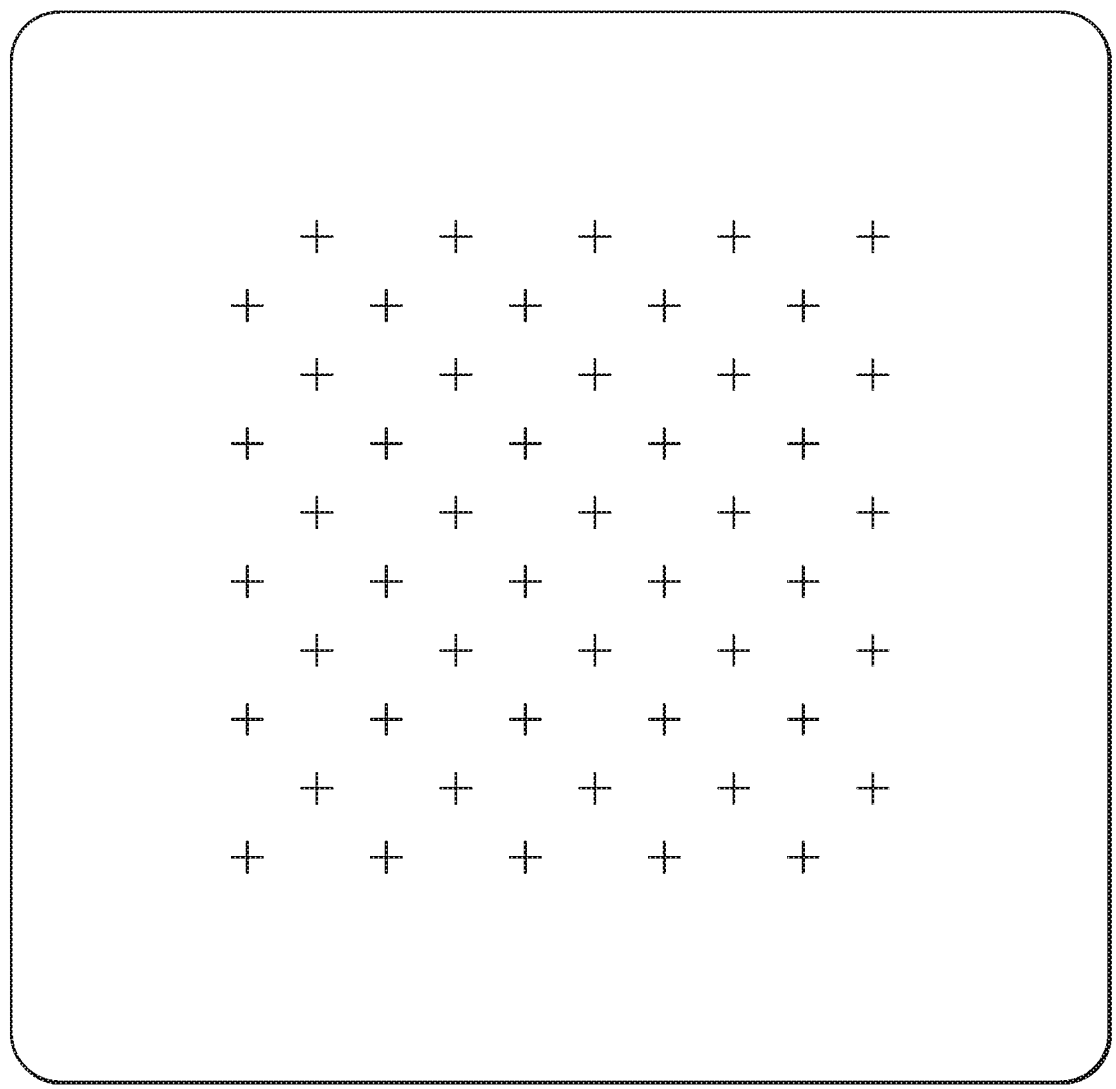
FIG. 13 is a schematic view of another example of another dressing layer, illustrating additional details that may be associated with some embodiments.

FIG. 12 and FIG. 13 illustrate other example configurations of the valves 1100, in which the valves 1100 each generally comprise a combination of intersecting slits or cross-slits. In some embodiments, shown in FIG. 12, the valves 1100 generally have a "Y" shape. In some embodiments, shown in FIG. 13, the valves 1100 generally have a cross or plus shape.

Figure 14:
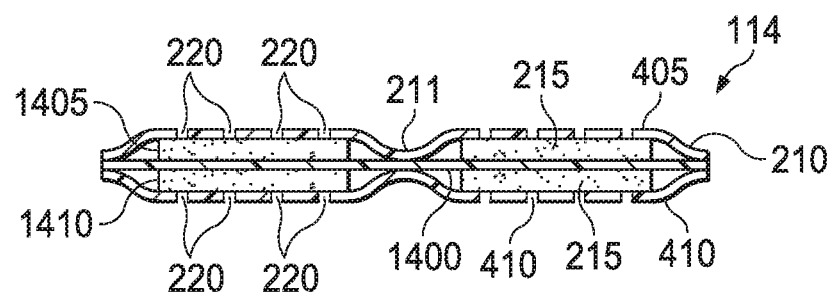
FIG. 14 is a schematic view of a dressing that may be associated with an example embodiment of the therapy system of FIG. 1.

FIG. 14 is a schematic section view of another example of the tissue interface 114 that may be associated with some embodiments of the therapy system of FIG. 1. In some embodiments, as shown in FIG. 14, the tissue interface 114 may include a first manifold layer 1405 and a second manifold layer 1410. The first manifold layer 1405 may be separated from the second manifold layer 1410 by an intermediate layer 1400. In some embodiments, the intermediate layer 1400 may comprise or consist essentially of a polymer film. As illustrated in the example of FIG. 14, the first layer 405 may be disposed adjacent to the first manifold layer 1405, opposite the intermediate layer 1400. The second layer 410 may be disposed adjacent to the second manifold layer 1410, opposite the intermediate layer 1400. The first layer 405 and the second layer 410 can enclose the first manifold layer 1405, the second manifold layer 1410, and the intermediate layer 1400 in some embodiments. The seams 210 can be formed between the first layer 405, the second layer 410, and the intermediate layer 1400 to enclose or form the manifold sections 215 in each of the first manifold layer 1405 and the second manifold layer 1410. Additional layers of manifold sections 215 and intermediate layers similar to intermediate layer 1400 may also be included in some embodiments. The fluid restrictions 220 can extend through each of the first layer 405 and the second layer 410.

In some embodiments, a method for treating a tissue site may include excising separable sections of a dressing based upon at least one of a size and shape of the tissue site being treated. The method may also include applying the dressing to fill and/or cover the tissue site, and sealing the dressing to epidermis adjacent to the tissue site. The method may further include fluidly coupling the dressing to a negative-pressure source, and applying negative pressure from the negative-pressure source to the dressing.

In some embodiments, excising separable sections may comprise cutting a seam or a seal between the separable sections. In some configurations, the separable sections may be excised without exposing a manifold section inside the dressing.

The systems, apparatuses, and methods described herein may provide significant advantages. For example, in some embodiments, the seams 210 may be wide enough to allow the interface sections 205 to be cut apart or otherwise separated so as to obtain a tissue interface 114 having a desired size and shape. For example, tissue interface 114 can be sized and shaped to fill deep and/or irregular wounds by separating the interface sections 205. Moreover, some embodiments of the dressing 104 may be worn for about 3 to about 10 days (e.g., about 7 days).

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
   a manifold comprising a first surface and a second surface opposite the first surface;
   a first layer adjacent to the first surface and a second layer adjacent to the second surface, the first layer and the second layer each comprising a polymer film;
   a plurality of fluid restrictions extending through both the first layer and the second layer such that the fluid restrictions in the first layer are substantially aligned with the fluid restrictions in the second layer across the manifold, and wherein one or more of the fluid restrictions is normally closed when unstrained and configured to open in response to a pressure gradient;
   a plurality of bonds between the first layer and the second layer, the plurality of bonds defining separable sections of the manifold; and
   at least one sacrificial joint positioned between each of the separable sections of the manifold, the sacrificial joint comprising a pair of triangular extensions joined at a common apex.

2. The dressing of claim 1, wherein the plurality of bonds form seams between the separable sections of the manifold, form a seal between the separable sections of the manifold, and/or comprise welds between the first layer and the second layer.

3. The dressing of claim 1, wherein the plurality of bonds form seams having a width of at least 2 millimeters and less than 5 millimeters between the separable sections of the manifold.

4. The dressing of claim 1, wherein the manifold comprises perforations aligned with the bonds and/or between the separable sections.

5. The dressing of claim 2, wherein the plurality of bonds form a seal between the separable sections of the manifold, the seal configured to be cut without exposing the manifold.

6. The dressing of claim 1, wherein the manifold has a thickness between 5 millimeters and 15 millimeters.

7. The dressing of claim 1, wherein the plurality of bonds define the separable sections as geometric shapes and/or tessellate shapes.

8. The dressing of claim 1, wherein the separable sections are equilateral polygons.

9. The dressing of claim 1, wherein the separable sections are equilateral polygons having sides not exceeding 20 millimeters and/or having an area less than 400 square millimeters.

10. The dressing of claim 1, further comprising a sealing layer adjacent to at least one of the first layer and the second layer, the sealing layer having apertures fluidly coupled to the fluid restrictions.

11. The dressing of claim 1, wherein the polymer film of one or both the first layer and the second layer is hydrophobic and/or has a substantially flat surface.

12. The dressing of claim 1, wherein the plurality of fluid restrictions comprise a plurality of slots, each of the slots having a length less than 4 millimeters and a width less than 2 millimeters.

13. The dressing of claim 1, wherein the plurality of fluid restrictions are coextensive with the manifold, are adjacent to the first surface and the second surface, and/or are distributed across the polymer film of one or both the first layer and the second layer in a uniform pattern.

14. The dressing of claim 13, wherein the uniform pattern comprises a grid of parallel rows and columns.

15. The dressing of claim 1, wherein:
   the plurality of fluid restrictions are distributed across the polymer film of one or both the first layer and the second layer in rows and columns that are mutually parallel;
   the rows are spaced about 3 millimeters on center; and
   the fluid restrictions in each of the rows are spaced about 3 millimeters on center.

16. The dressing of claim 1, wherein the plurality of fluid restrictions comprise or consist essentially of elastomeric valves in the polymer film of one or both the first layer and the second layer that are closed under atmospheric pressure.

17. The dressing of claim 16, wherein the elastomeric valves are fenestrations.

18. The dressing of claim 1, wherein the first layer is coextensive with the second layer.

19. An apparatus for providing negative-pressure treatment to a tissue site, the apparatus comprising:
   a manifold comprising a first surface and a second surface opposite the first surface;
   a first layer adjacent to the first surface and a second layer adjacent to the second surface, the first layer and the second layer each comprising a polymer film;
   a plurality of fluid restrictions extending through both the first layer and the second layer such that the fluid restrictions in the first layer are substantially aligned with the fluid restrictions in the second layer across the manifold, and wherein one or more of the fluid restrictions is normally closed when unstrained and configured to open in response to a pressure gradient;
   a plurality of bonds between the first layer and the second layer, the plurality of bonds defining separable sections of the manifold;
   at least one sacrificial joint positioned between each of the separable sections of the manifold, the sacrificial joint comprising a pair of triangular extensions joined at a common apex; and
   a negative-pressure source configured to be fluidly coupled to the manifold.

20. The apparatus of claim 19, wherein the plurality of bonds form seams having a width of at least 2 millimeters between the separable sections of the manifold.

21. The apparatus of claim 19, wherein the manifold comprises perforations aligned with the bonds and/or perforations between the separable sections.

22. The apparatus of claim 19, wherein the plurality of bonds form a seal between the separable sections of the manifold.

23. The apparatus of claim 19, wherein the plurality of bonds define the separable sections as geometric shapes and/or tessellate shapes.

24. The apparatus of claim 19, wherein the separable sections are equilateral polygons.

* * * * *